United States Patent
Okubo et al.

(10) Patent No.: US 6,229,037 B1
(45) Date of Patent: May 8, 2001

(54) POLYORGANOSILOXANE CATALYST

(75) Inventors: Tsuneyuki Okubo; Kazutoshi Matsu; Takao Araki, all of Osaka-fu; Toshihiro Takai, Hyogo-ken, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/543,157

(22) Filed: Apr. 4, 2000

(51) Int. Cl.$^7$ .................................................. C07F 7/08

(52) U.S. Cl. .................... 556/428; 502/158; 502/168; 528/30; 568/727

(58) Field of Search ................................. 502/158, 168; 556/428; 528/30; 568/727

(56) References Cited

U.S. PATENT DOCUMENTS 5,631,338  *  5/1997  Inoue et al. ..................... 556/428 X

* cited by examiner

*Primary Examiner*—Paul F. Shaver
(74) *Attorney, Agent, or Firm*—Burns, Doane, Swecker & Mathis, L.L.P.

(57) ABSTRACT

The invention provides a polyorganosiloxane catalyst with both of a sulfonic acid group-containing hydrocarbon group and a mercapto group-containing hydrocarbon group, wherein the total amount of the sulfonic acid group-containing hydrocarbon group and the mercapto group-containing hydrocarbon group is within a range of 0.3 to 2.0 $\mu$mol per unit surface area (1 $m^2$) of the polyorganosiloxane catalyst. The catalyst of the invention is highly active for the reaction to produce bisphenol A from acetone and phenol, with the deterioration of the catalyst under extreme suppression.

16 Claims, No Drawings

POLYORGANOSILOXANE CATALYST

BACKGROUND OF THE INVENTION

1. Field of the Invention

The present invention relates to a polyorganosiloxane catalyst, more specifically a polyorganosiloxane catalyst with both of a sulfonic acid group-containing hydrocarbon group and a mercapto group-containing hydrocarbon group. Such catalyst is used as the catalyst for producing bisphenol A by the dehydration-condensation of acetone and phenol.

2. Description of the Related Art

Bisphenol A [2,2-bis(4'-hydroxyphenyl)propane] is generally produced continuously in the mode of so-called flow reaction on fixed bed, comprising passing acetone and phenol of an excess of 8-fold to 15-fold in molar ratio to solid catalysts.

Conventionally, a technique using cation exchange resin or mercapto-modified cation exchange resins as such solid catalysts has been known, and in the mercapto-modified cation exchange resins, the mercaptoalkylamine are partially neutralized and mercapto group is fixed on cation exchange resins.

Concerning solid catalysts other than the ion exchange resin catalysts, additionally, a technique using polyorganosiloxane catalysts with both of a sulfonic acid group-containing hydrocarbon group and a mercapto group-containing hydrocarbon group as solid catalysts is described for example in U.S. Pat. No. 5,631,338, U.S. Pat. No. 5,789,628, EP-A-765,897, and EP-A-856,505. Compared with ion exchange resin catalysts, the polyorganosiloxane catalysts are known to have very high catalytic activity and selectivity.

These polyorganosiloxane catalysts are generally porous substances synthetically produced by so-called sol-gel process comprising hydrolysis of alkoxysilanes of different types and subsequent dehydration-condensation; and the porous substances comprise a macro-porous region of a pore size of 200 angstroms or more and a meso-porous region of a pore size within a range of 20 to 200 angstroms. The mean pore size in the meso-porous region is generally 20 to 100 angstroms. So as to recover high catalytic activity, generally, the specific surface area is 500 to 1500 $m^2/g$; and the total amount of the sulfonic acid group-containing hydrocarbon group and the mercapto group-containing hydrocarbon group is generally about 2.5 to 8.5 $\mu$mol per unit surface area (1 $m^2$).

In case that polyorganosiloxane catalysts are used for flow reaction on fixed bed to produce bisphenolA, additionally, it has been known that the catalyst life of the polyorganosiloxane catalysts can be prominently improved by adding a trace amount of water to the starting materials acetone and phenol, as in the case of the use of mercapto-modified cation exchange resin catalysts described in Japanese Patent Laid-open No. 172241/1994 for flow reaction on fixed bed.

However, the serious problem of the polyorganosiloxane catalysts, namely the continuous decrease of the catalytic activity thereof as the reaction time passes even by the addition of water to the raw materials, has not yet been overcome. Thus, the polyorganosiloxane catalysts have not yet been applied industrially.

As described above, the currently known polyorganosiloxane catalysts cannot be applied in practice because the deterioration of the catalysts, namely the continuous decrease of the catalytic activity as the reaction time passes, is serious. When such catalysts are charged as they are on fixed bed, problematically, the frequency of the exchange of the catalyst is increased, involving the elevation of the production cost of the resulting product, which is industrially disadvantageous.

Accordingly, it is a purpose of the invention to provide a catalyst with the deterioration thereof under suppression.

SUMMARY OF THE INVENTION

The present inventors have made investigations so as to overcome such problems. Consequently, the inventors have found that, by modifying the total amount (active site amount) of the sulfonic acid group-containing hydrocarbon group and the mercapto group-containing hydrocarbon group in a polyorganosiloxane catalyst with both of the sulfonic acid group-containing hydrocarbon group and the mercapto group-containing hydrocarbon group, unexpectedly, the reduction of the active site amount extremely suppresses the deterioration of the catalyst, with almost no deterioration of the high catalytic activity. More specifically, the inventors have found that by controlling the active site amount within an appropriate range per unit surface area of the polyorganosiloxane catalyst, the deterioration of the catalyst can significantly be suppressed, with no deterioration of the catalytic activity, so that bisphenol A can continuously be produced at a high yield and a high selectivity. Thus, the invention has been achieved.

That is, the invention relates to a polyorganosiloxane catalyst with both of a sulfonic acid group-containing hydrocarbon group and a mercapto group-containing hydrocarbon group, wherein the total amount of the sulfonic acid group-containing hydrocarbon group and the mercapto group-containing hydrocarbon group is regulated within a range of 0.5 to 2.0 $\mu$mol per unit surface area (1 $m^2$) of the polyorganosiloxane catalyst and a process for producing bisphenol A comprising the dehydration-condensation of acetone and phenol in the presence of said polyorganosiloxane catalyst.

DETAILED DESCRIPTION OF THE PREFERRED EMBODIMENTS

The polyorganosiloxane catalyst with a sulfonic acid group-containing hydrocarbon group and a mercapto group-containing hydrocarbon group in accordance with the invention means a polyorganosiloxane described in U.S. Pat. No. 5,631,338, EP-A-765,897, and EP-A-856,505, wherein the polyorganosiloxane is of a structure such that the sulfonic acid group-containing hydrocarbon group and the mercapto group-containing hydrocarbon group are partially bonded via carbon-silicon bonding or mercapto group-silicon bonding directly to the silicon atoms in the silica matrices comprising siloxane bonds.

Theoretically, the total amount (hereinafter referred to as active site amount) of the sulfonic acid group-containing hydrocarbon group and the mercapto group-containing hydrocarbon group in the polyorganosiloxane catalyst with both of the sulfonic acid group-containing hydrocarbon group and the mercapto group-containing hydrocarbon group can be modified up to about 8.00 mmol/g; however, a too large amount of the sulfonic acid group-containing hydrocarbon group makes the resulting polyorganosiloxane water soluble, so that the polyorganosiloxane can never be used as a solid catalyst. Furthermore, the increase of the active site amount induces great reduction of the specific surface area, with the resultant severe deterioration of the catalytic activity. So as to recover a polyorganosiloxane with a high catalytic activity, therefore, the total amount of the sulfonic acid group-containing hydrocarbon group and the mercapto group-containing hydrocarbon group, namely the active site amount, is generally 3.0 mmol/g or less. On a unit surface area basis, the value is converted to a range of 2.0 to 6.0 $\mu$mol/m$^2$ in case that the specific surface area is 500 to 1500 m$^2$/g.

In accordance with the invention, importantly, it is found that the catalytic life of the polyorganosiloxane catalyst can be improved while the high activity of the polyorganosiloxane catalyst is retained, by further reducing the active sites amount to a far lower value. More specifically, by controlling the active site amount within a range of 0.3 to 2.0 $\mu$mol/m$^2$, preferably within a range of 0.5 to 1.6 $\mu$mol/m$^2$, more preferably within a range of 0.6 to 1.3 $\mu$mol/m$^2$ per unit surface area of a polyorganosiloxane catalyst, the resulting polyorganosiloxane catalyst can retain a high catalytic activity while the deterioration thereof is suppressed. Additionally, the specific surface area of the catalyst is in no way with any specific limitation, but preferably, the specific surface area thereof is preferably within a range of 500 to 1500 m$^2$/g, more preferably within a range of 600 to 800 m$^2$/g.

In accordance with the invention, any hydrocarbon group with at least one sulfonic acid group (—SO$_3$H) can be used as the sulfonic acid group-containing hydrocarbon group, which is preferably a hydrocarbon group with one or more to 20 or less carbon atoms and with at least one sulfonic acid group-containing hydrocarbon group; the sulfonic acid group-containing hydrocarbon group is at least one hydrocarbon group selected from the group consisting of substituted or unsubstituted aromatic hydrocarbon groups with preferably 6 or more to 20 or less carbon atoms, more preferably 6 or more to 15 or less carbon atoms and with at least one sulfonic acid group (which are satisfactorily aromatic hydrocarbon groups with the aromatic groups therein being directly substituted with sulfonic acid group or aromatic hydrocarbon groups with the aromatic group-substituted hydrocarbon groups being substituted with sulfonic acid group) and substituted or unsubstituted aliphatic hydrocarbon groups (including alicyclic compounds) with preferably one or more to 15 or less carbon atoms, more preferably one or more to 10 or less carbon atoms and with at least one sulfonic acid group.

As examples of such sulfonic acid group-containing hydrocarbon group may be mentioned aromatic groups including phenyl group, tolyl group, naphthyl group, and methylnaphthyl group and being nuclearly substituted with at least one sulfonic acid group; aromatic group-substituted alkyl groups including benzyl group and naphthylmethyl group and being nuclearly substituted with at least one sulfonic acid group; alkyl groups such as methyl group, ethyl group, n-propyl group, isopropyl group, n-butyl group, isobutyl group, t-butyl group, linear or branched pentyl group, linear or branched hexyl group, linear or branched heptyl group, and linear or branched octyl group and being substituted with at least one sulfonic acid group; and cycloalkyl groups including cyclohexyl group, methylcyclohexyl group, and ethylcyclohexyl group and being substituted with at least one sulfonic acid group. Furthermore, these aromatic hydrocarbon groups or saturated or unsaturated aliphatic hydrocarbon (including alicyclic compounds) groups may be hydrocarbon groups with substituents such as halogen atom, alkoxyl group, nitro group and hydroxyl group.

The mercapto group-containing hydrocarbon group is at least one selected from hydrocarbon groups with one or more to 20 or less carbon atoms and with at least one mercapto group represented by the rational formula —SH, wherein the group —SH is bonded to aromatic hydrocarbon groups or saturated or unsaturated aliphatic hydrocarbon groups (including alicyclic compounds). Preferably, the mercapto group-containing hydrocarbon group is a hydrocarbon group wherein at least one —SH group is bonded to aromatic hydrocarbon groups or saturated aliphatic hydrocarbon groups.

Examples of such mercapto group-containing hydrocarbon group include mercapto-alkyl groups, for example mercaptomethyl group, 2-mercaptoethyl group, and 3-mercapto-n-propyl group; mercapto-alicyclic hydrocarbon groups, for example 4-mercaptocyclohexyl group and 4-mercaptomethylcyclohexyl group; and mercapto-aromatic hydrocarbon groups, for example p-mercaptophenyl group and p-mercaptomethylphenyl group. Preference is given to mercaptomethyl group and mercaptopropyl group; particularly, mercaptomethyl group is excellent in terms of the catalytic activity and the duration of the catalytic activity. Furthermore, these aromatic or aliphatic or alicyclic hydrocarbon groups containing mercapto group may be hydrocarbon groups with substituents such as halogen atom, alkoxyl group, nitro group and hydroxyl group, in addition to mercapto group.

In the inventive polyorganosiloxane catalyst with the sulfonic acid group-containing hydrocarbon group and the mercapto group-containing hydrocarbon group, the molar ratio of the sulfonic acid group-containing hydrocarbon group to the mercapto group-containing hydrocarbon group is in no way with specific limitation, but the molar ratio is preferably 0.5 to 1.5:0.5 to 1.5, more preferably 1:1 as the sulfonic acid group-containing hydrocarbon group: the mercapto group-containing hydrocarbon group in molar quantity.

Such polyorganosiloxane catalyst can be produced by the following processes:
So-called sol-gel processes, including
(1) a process comprising mixing together alkoxysilane with a sulfonic acid group-containing hydrocarbon group, alkoxysilane with a mercapto group-containing hydrocarbon group and tetraalkoxysilane at an arbitrary ratio, hydrolyzing the resulting mixture and subjecting the resulting product to co-condensation; and
(2) a process comprising mixing together a water-soluble hydrolyzate of alkoxysilane with a sulfonic acid group-containing hydrocarbon group, alkoxysilane with a mercapto group containing hydrocarbon group and tetraalkoxysilane at an arbitrary ratio, hydrolyzing the resulting mixture and subjecting the resulting product to co-condensation; and so-called silylation process, including
(3) a process comprising silylating alkoxysilane with a mercapto group-containing hydrocarbon group to support the mercapto group onto the silanol group present in a polyorganosiloxane with a sulfonic acid group-containing hydrocarbon group.

The aforementioned active site amount can readily be adjusted by controlling the amount of alkoxysilane used as a starting material when producing the catalyst.

For the sol-gel process of polyorganosiloxane, for example, a polyorganosiloxane with a high specific surface area of generally 500 to 600 m$^2$/g can be produced, by using aqueous ammonia as a base catalyst during hydrolysis. During the preparation, additionally, the parent material tetraalkoxysilane is mixed at a ratio of 10 to 80 in molar ratio to the total molar number of alkoxysilane with the sulfonic acid group-containing hydrocarbon group and alkoxysilane with the mercapto group-containing hydrocarbon group, followed by addition of water and subsequent hydrolysis and dehydration-condensation, to prepare a polyorganosiloxane catalyst at a desired active site amount.

The polyorganosiloxane catalyst thus prepared is of a mean pore size of at least 25 to 85 angstroms, more strictly 30 to 70 angstroms, in the mesoporous region with a pore size range of 20 to 200 angstroms.

The polyorganosiloxane catalyst recovered by the method described above is so fragile and readily degraded that the polyorganosiloxane catalyst is problematic for use in practical sense. When such catalyst is charged as it is on a fixed bed, problems such as flow blocking at the outlet of a reactor emerge. By conventional molding methods of catalysts using binders and the like and requiring sintering process at high temperature, organic functional groups such as mercapto group and sulfonic acid group are deteriorated. Accordingly, the methods can never be used.

So as to overcome the problem, it is proposed that a powdery polyorganosiloxane with both of a sulfonic acid group-containing hydrocarbon group and a mercapto group-containing hydrocarbon group and with the aforementioned active site amount, is supported on a porous molded material. In such manner, a polyorganosiloxane catalyst with no emergence of any problem such as the occlusion of reactor conduit can be recovered, with no use of the conventional molding methods using binders and the like and requiring high-temperature processing.

The porous molded material to be used in accordance with the invention comprises a material inert to chemical substances in the reactor and the reaction conditions. The molded material satisfying the conditions includes for example active charcoal, silica gel, silica-alumina, alumina, molecular sieve, titania, silica-titania, zirconia, and zeolite. Among them, silica gel is particularly preferably used.

As to the particle size of such porous molded material, the porous molded material is used as it is, with no specific limitation. 90% of the total amount is of a particle size preferably within a range of 30 $\mu$m to 5 cm, more preferably within a range of 30 $\mu$m to 1 cm. The specific surface area is with no specific limitation but is preferably within a range of 2 to 1100 $m^2$/g, more preferably within a range of 50 to 600 $m^2$/g. In accordance with the invention, additionally, the pore volume is with no specific limitation, but is preferably within a range of 0.05 to 5.0 ml/g and is more preferably within a range of 0.3 to 3.0 ml/g. Still furthermore, in accordance with the invention, the pore size is with no specific limitation, but is preferably 3 angstroms or more, more preferably within a range of 5 to 1000 angstroms.

As to the shape of such porous molded material, porous materials in any single shape of cylinder, sphere, doughnut, honeycomb, a disrupted material with a uniform particle size, square and tube can preferably be used.

As to the method for supporting the polyorganosiloxane on the porous molded material to prepare a supported catalyst, the following methods can be used to prepare the supported catalyst, but the polyorganosiloxane-supported catalyst for use in accordance with the invention is not limited only to these methods. As readily preparative methods, for example, (1) a process comprising mixing together alkoxysilane with a sulfonic acid group-containing hydrocarbon group, alkoxysilane with a mercapto group-containing hydrocarbon group and tetraalkoxysilane at an arbitrary ratio, hydrolyzing the resulting mixture and subjecting the resulting product to co-condensation, wherein the resulting polyorganosiloxane is impregnated and supported on the porous molded material at a liquid state; and (2) a process comprising mixing together a hydrolyzate of alkoxysilane with a water-soluble sulfonic acid group-containing hydrocarbon group, alkoxysilane with a mercapto group-containing hydrocarbon group, and tetraalkoxysilane, at an arbitrary ratio, hydrolyzing the resulting mixture and subjecting the resulting product to co-condensation, wherein the resulting polyorganosiloxane is impregnated and supported on the porous molded material at a liquid state.

The inventive polyorganosiloxane catalyst with a sulfonic acid group-containing hydrocarbon group and with a mercapto group-containing hydrocarbon group can be used for the reaction for the production of bisphenol A from acetone and phenol. For example, the reaction is promoted, using a fixed bed flow reaction system filled with the polyorganosiloxane catalyst, as the reactor for bisphenol A production. The retention time in this case is with no specific limitation, but generally, the retention time is one minute to 15 hours, preferably 10 minutes to 5 hours. The ratio of the starting materials phenol and acetone to be used is with no specific limitation, but it is recommended to promote the reaction at a molar ratio of phenol to acetone within a range of preferably 2 to 50, more preferably 4 to 25. In case that the amount of phenol is too small, it is difficult to attain a high conversion ratio of the raw material acetone. In case that the amount of phenol is too much, a high acetone conversion ratio can be attained, but the use of phenol more than necessary requires a very large reactor and additionally requires massive circulation of phenol, uneconomically. In accordance with the invention, the reaction temperature is with no specific limitation but is preferably within a range of 40 to 200° C., more preferably within a range of 50 to 120° C. In case that the reaction temperature is too low, an extremely long reaction time is required so as to attain a high conversion ratio of the raw material, leading to the decrease of the productivity. In case that the reaction temperature is too high, undesirable side reactions progress, so that the reaction selectivity is decreased, uneconomically.

EXAMPLES

The invention is now described specifically in the following examples. However, the examples are simply illustrated, not for limitation of the invention. In the examples, additionally, the catalyst life is expressed as deterioration ratio in 300 hours (value obtained by dividing the difference between the acetone conversion ratio on hour 20 after reaction and the acetone conversion ratio on hour 300 after reaction with the acetone conversion ratio on hour 20 after reaction). Given that the deterioration ratio of a catalyst with an active site amount of more than 2 $\mu$mol/$m^2$ per unit surface area (Comparative Examples 1 and 2) is designated 100, then, the deterioration ratio of a corresponding catalyst is expressed as relative value (value obtained by dividing the deterioration ratio value of a catalyst with the deterioration ratio value of the catalyst with the active site amount of more than 2 $\mu$mol/$m^2$ and multiplying the resulting divided value with 100); when the relative value is 60 or less, it is determined that the deterioration is suppressed.

Furthermore, the amount of the sulfonic acid group in the polyorganosiloxane was measured according to a general method for measuring solid acids. More specifically, the polyorganosiloxane was subjected to ion exchange with an aqueous sodium chloride solution at about 10-fold moles the amount of the sulfonic acid group at room temperature; the released hydrochloric acid was titrated with an aqueous sodium hydroxide solution, to calculate the amount of the sulfonic acid group. Additionally, the amount of mercapto group was calculated by treating the polyorganosiloxane with an excess of aqueous iodide solution and titrating the remaining iodide with aqueous sodium thiosulfate solution.

(1) Synthesis of Sulfonic Acid Group-Containing Alkoxysilane

In a round-bottom two-necked 500-ml flask with a dropping funnel was placed methylene chloride of 200 ml, followed by addition of phenyltrichlorosilane of 124.02 g (0.585mol) under cooling on ice. To the resulting mixture was dropwise added a solution of sulfuric acid anhydride of 46.80 g (0.585 mol) dissolved in 100 ml of methylene chloride in nitrogen stream over 30 minutes; thereafter, the ice bath was drawn out; and the resulting mixture was stirred at room temperature for one hour, for sulfonation. The dropping funnel was removed. The mixture was heated in nitrogen stream to 100° C., using an oil bath, to distill off methylene chloride.

Subsequently, 161.50 g of ethanol was dropwise added in nitrogen stream over 2 hours for ethoxylation, while hydrogen chloride was removed. The resulting ethanol solution of 238.60 g of the phenylsulfonic acid group-containing ethoxysilane with impurities was used as a raw material for the sulfonic acid component for the sol-gel preparation of a polyorganosiloxane catalyst with sulfonic acid group-containing hydrocarbon group and mercapto group-containing hydrocarbon group.

(2) Preparation of Polyorganosiloxane Catalyst

Catalyst 1

In a round-bottom two-necked 500-ml flask with a stirrer bar were placed the ethanol solution (17.59 g; 21.39 mmol) of the sulfonic acid group-containing ethoxysilane, as recovered in (1), tetraethoxysilane (159.74 g; 766.77 mmol), mercaptomethyltrimethoxysilane (3.60 g; 21.39 mmol) and ethanol (150 ml); and the resulting mixture was mixed together, followed by dropwise addition of water of 28.8 g over 30 minutes. Subsequently, the resulting mixture was heated and stirred at 65° C. for 4 hours. After the mixture was left to stand for cooling, an aqueous solution of a mixture of 10 ml of aqueous 28% ammonia and 69.1 ml of water was dropwise added to the mixture, for 4-hr agitation at room temperature. The resulting mixture was agitated at 65° C. for 3 days for aging, which was then subjected to distillation under reduced pressure with an evaporator, to recover a white solid. Then, a procedure of addition of 300 ml of 2N hydrochloric acid and agitation at room temperature for 30 minutes was repeated twice, so that the solid was returned to proton type. A procedure of filtration and subsequent rinsing in 300 ml of ion exchange water was repeated twice, to remove hydrochloric acid. Finally, the resulting product was dried at 100° C. under reduced pressure for 6 hours.

By the aforementioned procedures, the polyorganosiloxane with the sulfonic acid group-containing hydrocarbon group and the mercapto group-containing hydrocarbon group was recovered at a yield of 56.3 g and was then designated catalyst 1. The amount of the sulfonic acid group in the catalyst 1 was measured, which was 0.38 meq/g. Additionally, the specific surface area was measured by the gas adsorption method according to the BET method, which was 662 m$^2$/g. The active site amount per unit surface area (1 m$^2$) was 1.15 $\mu$mol.

Catalyst 2

The preparation of polyorganosiloxane catalyst 2 was carried out under the conditions in Table 1, by the same method as for the preparation of the catalyst 1. The results are shown in Table 1.

Catalysts 3 to 5

The preparation of polyorganosiloxane catalysts 3 to 5 was carried out under the conditions in Table 1 by the same method as for the preparation of the catalyst 1, except that mercaptomethyltrimethoxysilane was replaced with mercaptopropyltrimethoxysilane. The results are shown in Table 1.

(3) Preparation of Polyorganosiloxane-Supported Catalyst

Catalyst 6

In a round-bottom two-necked 500-ml flask with a stirrer were placed the ethanol solution (9.25 g) of the phenylsulfonic acid group-containing ethoxysilane, as recovered in (1), tetraethoxysilane (84.0 g; 0.40 mmol), mercaptopropyltrimethoxysilane (2.20 g; 11.24 mmol), and ethanol (80 ml); and the resulting mixture was mixed together.

To the resulting mixture was dropwise added water of 15.1 g (838.89 mmol) over 30 minutes. To the resulting solution was charged a commercially available silica gel particle of 55 g (CARiACT Q-15 of particle size of 0.85 to 1.70 mm; manufactured by Fuji Silysia Chemicals, Co. Ltd.). The resulting mixture was heated and agitated at 65° C. for 3 hours. After the mixture was left to stand for cooling, followed by distillation under reduced pressure with rotary evaporator, the resulting polyorganosiloxane was supported on the silica gel particle.

Subsequently, an aqueous solution of a mixture of 5 ml of aqueous 28% ammonia and 35 ml of water was dropwise added to the resulting silica gel, followed by agitation at room temperature for 4 hours. For aging, the mixture was further agitated at 65° C. for 3 days. The resulting mixture was again subjected to distillation under reduced pressure with a rotary evaporator. The silica gel particle was transferred into a 1000-ml beaker, followed by addition of 200 ml of 2N hydrochloric acid and agitation at room temperature for 30 minutes, so that the silica gel returned to the proton type. After separation by filtration, rinsing in 500 ml of ion exchange water was repeated twice, to remove hydrochloric acid.

Finally, the resulting product was dried at 100° C. under reduced pressure for 4 hours. By the aforementioned procedures, the silica gel particle supporting the polyorganosiloxane with the sulfonic acid group-containing hydrocarbon group and the mercapto group-containing hydrocarbon group was recovered at a yield of 84.6 g. The amount of the polyorganosiloxane supported on the silica gel particle was at 35% by weight in the supported catalyst 6. Additionally, the amount of the sulfonic acid group in the supported catalyst 6 was measured, which was 0.13 meq/g.

Catalyst 7

Polyorganosiloxane catalyst 7 was recovered in the same manner as for the catalyst 6, except for no use of the silica gel particle as the carrier.

Catalyst 8

Supported catalyst 8 was recovered in the same manner as for the catalyst 6, except that the particle size of the silica gel particle as the carrier was 75 to 500 $\mu$m. The amount of the sulfonic acid group in the catalyst 8 was measured, which was 0.14 meq/g.

Catalyst 9

Supported catalyst 9 was recovered in the same manner as for the catalyst 6, except that the silica gel particle as the carrier was replaced with silica-alumina. The amount of the sulfonic acid group in the catalyst 9 was measured, which was 0.12 meq/g.

Catalyst 10

The catalyst 17 in the example of U.S. Pat. No. 5,631,338 was prepared as follows. In a three-necked 1000-ml flask with an agitator are placed phenyltriethoxysilane (36.06 g; 0.15 mol), tetraethoxysilane (72.92 g; 0.35 mol), and ethanol (62.5 ml), followed by drop wise addition of 0.01N hydrochloricacid (16.7 ml). The solution is heated to 80 to 90° C. in an open system for concentration. By concentration until no ethanol is evaporated, a liquid at a very high viscosity is recovered. The liquid was left to stand for cooling, followed by addition of 15 ml of hexane and 22.5 ml of ethanol and subsequent dropwise addition of a mixture of 25 ml of aqueous 28% ammonia and 135 ml of water; and the resulting mixture was agitated at room temperature for 4 hours. The resulting product was separated by filtration, rinsed in a large volume of water, and dried in a hot-air dryer at 120° C. for 10 hours, so that a white solid of 40.4 g was recovered. To 10.0 g of the polyorganosiloxane with phenyl group in the silica matrix was added 100 ml of conc. sulfuric acid, and the resulting mixture was agitated at 80° C. for 3 hours. After the mixture was left to stand for cooling, the resulting solid was separated by filtration, rinsed in a large volume of water, and dried in a hot-air dryer at 120° C. for 10 hours, so that a polyorganosiloxane with sulfonic acid group was recovered at a yield of 10.5 g. 6.0 g (0.86 mmol/g acidamount) of the polyorganosiloxane with sulfonic acid group was ion exchanged to $Na^+$ type by using aqueous sodium chloride solution. The resulting polyorganosiloxane was dried at 120° C. under reduced pressure for 4 hours, followed by addition of 10 g of mercaptopropyltrimethoxysilane$_3$ and subsequent agitation at 100° C. for 4 hours for silylation. The silylated polyorganosiloxane was separated by filtration, rinsed in methanol and ion exchanged to acid type, by using 2 N hydrochloric acid of 300 ml; subsequently, the resulting product was rinsed in a large amount of water, to discard the residual hydrochloric acid. The product was further dried under reduced pressure at 100° C. for 6 hours, to recover polyorganosiloxane catalyst 10 with sulfonic acid group and mercapto group at a yield of 6.8 g. The specific surface area thereof was measured by gas adsorption method according to the BET method, which was 200 $m^2/g$. The active site amount per unit surface area (1 $m^2$) was 5.1 $\mu$mol.

TABLE 1

| Component | Catalyst | | | | | |
|---|---|---|---|---|---|---|
| | 1 | 2 | 3 | 4 | 5 | 10 |
| Sulfonic acid component (mmol) | 21.39 | 40.13 | 21.39 | 21.39 | 40.13 | — |
| TEOS (mmol) | 766.77 | 266.72 | 756.79 | 1515.23 | 247.98 | — |
| MMTMS (mmol) | 21.39 | 40.13 | — | — | — | — |
| MPTMS (mmol) | — | — | 21.39 | 21.39 | 40.13 | — |
| Ethanol(ml) | 150 | 150 | 150 | 150 | 150 | — |
| Added water in acidic condition (g) | 28.8 | 11.8 | 28.4 | 55.8 | 11.1 | — |
| Added water in basic condition (g) | 69.1 | 28.3 | 68.2 | 133.8 | 26.7 | — |
| Formed catalyst (g) | 56.3 | 35.2 | 56.3 | 101.9 | 35.2 | — |
| Amount of solid acid(meq/g) | 0.38 | 1.14 | 0.38 | 0.21 | 1.14 | 0.86 |
| Specific surface area($m^2$/g) | 662 | 723 | 721 | 705 | 710 | 200 |
| Average pore size of mesoporous region (Å) | 40 | 23 | 38 | 55 | 21 | 70 |
| Pore volume of meso-porous region (ml/g) | 0.66 | 0.39 | 0.70 | 1.00 | 0.39 | 0.70 |
| Active site amount ($\mu$mol/$m^2$) | 1.15 | 3.15 | 1.05 | 0.60 | 3.21 | 5.10 |

TEOS; tetraethoxysilane
MMTMS; mercaptomethyltrimethoxysilane
MPTMS; mercaptopropyltrimethoxysilane (4) Preparation of Bisphenol A Example 1

The polyorganosiloxane catalyst 1 (26.7 g; 49.2 cc) (total amount of active site: 20.3 mmol) was charged in a cylindrical reactor (2.2-cm diameter and 40-cm length). From the bottom of the reactor, a mixture of phenol, acetone, and water at a molar ratio of 5:1:0.4 was passed at a velocity of 20.00 g/hr through the catalyst. The reaction temperature was 100° C. The reaction product recovered in 20 hours was analyzed by liquid chromatography. Consequently, the acetone conversion ratio was 88%, while the selectivity of bisphenol A species ([2,2-bis(4'-hydroxyphenyl)propane], [2-(2'-hydroxyphenyl)-2-(4'-hydroxyphenyl)propane]) was 92%.

In the same manner, the reaction product recovered in 300hours was analyzed by liquid chromatography. Consequently, the acetone conversion ratio was 85%, while the catalyst deterioration ratio indicating the catalyst life, as calculated by the aforementioned method, was 3.4% in 300hours; and the relative value of the deterioration ratio was 22.8, given that the Comparative Example 1 was defined 100. The results are shown in Table 2.

Comparative Example 1

The Example 1 was followed, except that 8.9 g (16.4 cc) of the polyorganosiloxane catalyst 2 was charged in the cylindrical reactor, so that the total amount of the active site thereof was equal to the total amount of the active site in the Example 1. The results are shown in Table 2.

TABLE 2

| | Example 1 | Comparative Example 1 |
|---|---|---|
| Catalyst | 1 | 2 |
| Amount of catalyst (g) | 26.7 | 8.9 |
| Total amount of active site (mmol) | 20.3 | 20.3 |
| Active site amount ($\mu$mol/$m^2$) | 1.15 | 3.15 |
| Conversion of acetone (%, 20 h/300 h) | 88/85 | 67/74 |
| Selectivity of BPAs (%, 20 h) | 92 | 91 |
| Deterioration ratio of catalyst (300 h) | 3.4 | 14.9 |

TABLE 2-continued

|  | Example 1 | Comparative Example 1 |
|---|---|---|
| Relative value of deterioration ratio (300 h) | 22.8 | 100 |

Example 2

The Example 1 was followed, except that 26.7 g (49.2 cc) of the polyorganosiloxane catalyst 3 was charged in the cylindrical reactor, so that the total amount of the active site of the polyorganosiloxane catalyst was adjusted to 20.3 mmol. The results are shown in Table 3.

Example 3

The Example 2 was followed, except that 48.4 g (89.2 cc) of the polyorganosiloxane catalyst 4 was charged in the cylindrical reactor, so that the total amount of the active site thereof was equal to the total amount of the active site in the Example 2. The results are shown in Table 3.

Comparative Example 2

The Example 2 was followed, except that 8.9 g (16.4 cc) of the polyorganosiloxane catalyst 5 was charged in the cylindrical reactor, so that the total amount of the active site thereof was equal to the total amount of the active site in the Example 2. The results are shown in Table 3.

Comparative Example 3

The Example 2 was followed, except that 19.9 g (37 cc) of the polyorganosiloxane catalyst 10 was charged in the cylindrical reactor, so that the total amount of the active site thereof was equal to the total amount of the active site in the Example 2. The results are shown in Table 3.

TABLE 3

|  | Example 2 | Example 3 | Comparative Example 2 | Comparative Example 3 |
|---|---|---|---|---|
| Catalyst | 3 | 4 | 5 | 10 |
| Amount of catalyst (g) | 26.7 | 48.4 | 8.9 | 19.9 |
| Total amount of active site (mmol) | 20.3 | 20.3 | 20.3 | 20.3 |
| Active site amount ($\mu mol/m^2$) | 1.05 | 0.60 | 3.21 | 5.10 |
| Conversion of acetone (%, 20 h/300 h) | 82/73 | 69/58 | 87/62 | 83/20 |
| Selectivity of BPAs (%, 20 h) | 92 | 92 | 91 | 90 |
| Deterioration ratio of catalyst (300 h) | 11.0 | 15.9 | 28.7 | 75.9 |
| Relative value of deterioration ratio (300 h) | 38.3 | 55.4 | 100 | 264.5 |

Example 4

The supported catalyst 6 of 78.0 g (140 cc) was charged in a cylindrical reactor (2.2-cm diameter and 40-cm length) with 20-$\mu$m upper and lower filters. From the bottom of the reactor, a mixture of phenol, acetone, and water at a molar ratio of 5:1:0.4 was passed at a velocity of 21.3 g/hr through the catalyst 6. The reaction temperature was 100° C. The reaction product recovered in 21 hours was analyzed by liquid chromatography. Consequently, the acetone conversion ratio was 49%, while the selectivity of bisphenol A species ([2,2-bis(4'-hydroxyphenyl)propane], [2-(2'-hydroxyphenyl)-2-(4'-hydroxyphenyl)propane]) was 90%.

In the same manner, the reaction product recovered in 280 hours was analyzed by liquid chromatography. Consequently, the acetone conversion ratio and the selectivity of bisphenol A species were retained at 43% and 92%, respectively. Additionally, the flow rate of the raw material mixture was scarcely changed at 21.1 g/hr, with almost no degradation of the supported catalyst 6 due to fine pulverization. The reaction was terminated at this timing. The acid amount in the supported catalyst 6 recovered was measured. Consequently, the acid amount was the same as the amount prior to use, which was 0.28 meq/g. Thus, no dissociation of the active component of the supported catalyst from the carrier was observed.

Comparative Example 4

The Example 4 was followed, using the catalyst 7 of 26.7 g. On hour 20 after the start of the reaction, the flow rate of the raw material mixture was decreased to 18 g/hr; on hour 240, the flow rate of the raw material mixture was markedly decreased to 14 g/hr. Thus, the reaction was terminated then. The cylindrical reactor was opened. The filters were partially occluded under observation.

Example 5

The Example 4 was followed, using the supported catalyst 8. A mixture of phenol, acetone, and water was passed at a velocity of 22.2 g/hr through the catalyst 8. The reaction product recovered 20 hours after the start of the reaction was analyzed in the same manner. Consequently, the acetone conversion ratio and the selectivity of bisphenol A species ([2,2-bis(4'-hydroxyphenyl)propane], [2-(2'-hydroxyphenyl)-2-(4'-hydroxyphenyl)propane]) were 78% and 93%, respectively.

In the same manner, the reaction product recovered 280 hours after the start of the reaction was analyzed in the same manner. Consequently, the acetone conversion ratio and the selectivity of bisphenol A species were retained at 60% and 93%, respectively. Additionally, the flow rate of the raw material mixture then was scarcely changed at 22.0 g/hr, with almost no degradation of the supported catalyst 8 due to fine pulverization. The reaction was terminated at this timing. The acid amount in the supported catalyst 8 recovered was measured. Consequently, the acid amount was the same as the amount prior to use, which was 0.14 meq/g. Thus, no dissociation of the active component of the supported catalyst 8 from the carrier was observed.

Example 6

The Example 4 was followed, except for the use of the supported catalyst 9. A mixture of phenol, acetone, and water was passed at a velocity of 21.8 g/hr through the catalyst 9. The reaction product recovered 20 hours after the start of the reaction was analyzed in the same manner. Consequently, the acetone conversion ratio and the selectivity of bisphenol A species ([2,2-bis(4'-hydroxyphenyl)propane], [2-(2'-hydroxyphenyl)-2-(4'-hydroxyphenyl)propane]) were 47% and 90%, respectively.

In the same manner, the reaction product recovered 280 hours after the start of the reaction was analyzed in the same manner. Consequently, the acetone conversion ratio and the selectivity of bisphenol A species were retained at 41% and 90%, respectively. Additionally, the flow rate of the raw material mixture was scarcely changed at 21.3 g/hr, with almost no degradation of the supported catalyst 9 due to fine pulverization. The reaction was terminated at this timing. The acid amount in the supported catalyst 9 recovered was measured. Consequently, the acid amount was the same as the amount prior to use, which was 0.12 meq/g. Thus, no dissociation of the active component of the supported catalyst 9 from the carrier was observed.

EFFECT OF THE INVENTION

Based on the inverse idea of the reduction of the active site amount, the inventive method enables the production of a polyorganosiloxane catalyst with high activity and long life. Furthermore, a reliable catalyst which does not cause occurrence of conduit occlusion in any fixed bed reactor can be recovered, by supporting the catalyst on porous molded materials. Consequently, bisphenol A can be produced, significantly preferentially in terms of processability and economy, from the dehydration-condensation of acetone and phenol, using the catalyst.

What is claimed is:

1. A polyorganosiloxane catalyst with both of a sulfonic acid group-containing hydrocarbon group and a mercapto group-containing hydrocarbon group, wherein the total amount of the sulfonic acid group-containing hydrocarbon group and the mercapto group-containing hydrocarbon group is within a range of 0.3 to 2.0 $\mu$mol per unit surface area (1 m$^2$) of the polyorganosiloxane catalyst.

2. The polyorganosiloxane catalyst according to claim 1, wherein the specific surface area is 500 to 1500 m$^2$/g.

3. The polyorganosiloxane catalyst according to claim 1, wherein the mercapto group-containing hydrocarbon group is mercaptomethyl group or mercaptopropyl group.

4. The polyorganosiloxane catalyst according to claim 3, wherein the mercapto group-containing hydrocarbon group is mercaptomethyl group.

5. The polyorganosiloxane-supported catalyst comprising a polyorganosiloxane according to claim 1 being supported on a porous molded material.

6. The polyorganosiloxane-supported catalyst according to claim 5, wherein the porous molded material is silica gel or silica-alumina.

7. The polyorganosiloxane-supported catalyst according to claim 6, wherein the porous molded material is silica gel.

8. The polyorganosiloxane-supported catalyst according to claim 5, wherein 90% or more of the total amount of the porous molded material is of the particle size of 30 $\mu$m to 5 cm.

9. The process for producing bisphenol A, comprising the dehydration-condensation of acetone and phenol in the presence of a polyorganosiloxane catalyst according to claim 1.

10. The process for producing bisphenol A, comprising the dehydration-condensation of acetone and phenol in the presence of a polyorganosiloxane catalyst according to claim 2.

11. The process for producing bisphenol A, comprising the dehydration-condensation of acetone and phenol in the presence of a polyorganosiloxane catalyst according to claim 3.

12. The process for producing bisphenol A, comprising the dehydration-condensation of acetone and phenol in the presence of a polyorganosiloxane catalyst according to claim 4.

13. The process for producing bisphenol A, comprising the dehydration-condensation of acetone and phenol in the presence of a polyorganosiloxane-supported catalyst according to claim 5.

14. The process for producing bisphenol A, comprising the dehydration-condensation of acetone and phenol in the presence of a polyorganosiloxane-supported catalyst according to claim 6.

15. The process for producing bisphenol A, comprising the dehydration-condensation of acetone and phenol in the presence of a polyorganosiloxane-supported catalyst according to claim 7.

16. The process for producing bisphenol A, comprising the dehydration-condensation of acetone and phenol in the presence of a polyorganosiloxane-supported catalyst according to claim 8.

* * * * *